United States Patent [19]
Nelson et al.

[11] Patent Number: 6,002,133
[45] Date of Patent: Dec. 14, 1999

[54] SERVICEABLE ABSORBENT FOR GAS SPECTROMETER INTERIOR

[75] Inventors: Shari Nelson; G. Lamar Kirchhevel, both of Westminster, Colo.

[73] Assignee: Datex-Ohmeda, Inc., Tewksbury, Mass.

[21] Appl. No.: 08/915,494

[22] Filed: Aug. 19, 1997

[51] Int. Cl.[6] ................................................ G01N 21/35
[52] U.S. Cl. ............................... 250/343; 250/339.13
[58] Field of Search ................................. 250/343, 339.13

[56] References Cited

U.S. PATENT DOCUMENTS

| | | |
|---|---|---|
| 4,446,869 | 5/1984 | Knodle . |
| 4,485,822 | 12/1984 | O'Connor . |
| 4,546,778 | 10/1985 | Sullivan . |
| 4,679,573 | 7/1987 | Parnoff . |
| 4,821,737 | 4/1989 | Nelson . |
| 4,886,528 | 12/1989 | Aaltonen . |
| 4,924,860 | 5/1990 | Larsen . |
| 5,042,500 | 8/1991 | Norlien . |
| 5,091,649 | 2/1992 | Rantala ................................. 250/343 |
| 5,233,996 | 8/1993 | Coleman . |
| 5,293,875 | 3/1994 | Stone . |
| 5,357,971 | 10/1994 | Sheehan . |
| 5,365,938 | 11/1994 | Eskelä . |
| 5,404,885 | 4/1995 | Sheehan . |
| 5,464,982 | 11/1995 | Drucker et al. ........................ 250/343 |
| 5,801,384 | 9/1998 | Kirchhevel ............................ 250/343 |

*Primary Examiner*—Constantine Hannaher
*Attorney, Agent, or Firm*—Holme Roberts & Owen, LLP

[57] ABSTRACT

A gas spectrometer is provided having an enhanced capability for maintaining initial calibration conditions therewithin. The gas spectrometer is particularly apt for respiratory gas analysis applications and includes a housing assembly that defines an internal containment area(s), within which a radiation source, optical assembly, sample gas assembly and radiation detection assembly are positioned. A gas removal assembly is provided for removing one or more undesired gas component types from within the internal containment area during field use. The gas removal assembly is selectively retractable from the housing assembly to permit periodic servicing (e.g., replacement of $CO_2$ absorbent) without requiring disassembly or recalibration of the spectrometer.

16 Claims, 4 Drawing Sheets

SERVICEABLE ABSORBENT FOR GAS SPECTROMETER INTERIOR

FIELD OF THE INVENTION

This invention relates to gas spectrometers for measuring the concentration of predefined components of a gas sample, and is particularly apt for use in respiratory gas spectrometers for measuring the concentration of oxygen, $CO_2$ and/or one or more anesthetic agents in a respiratory gas stream sample.

BACKGROUND OF THE INVENTION

Gas spectrometers are utilized in a wide variety of industrial and medical applications to monitor the presence and concentration of one or more predefined components in a gas sample. Typically, light of a known spectral content is directed through a gas sample and the intensity of the transmitted light at a number of different center-wavelengths is detected. By utilizing known light absorption characteristics of the predefined gas components at the center-wavelengths, the detected light intensities provide a basis to determine, via statistical processing, the concentrations of the predefined components. As will be appreciated, it is important that the initial calibration conditions of the spectrometer be maintained in order to accurately relate the measured light intensities to gas component concentrations.

This is particularly true in respiratory gas spectrometers for measuring the concentration of carbon dioxide and/or oxygen, and one or more anesthetic agents such as nitrous oxide, halothane, enflurane, isoflurane, sevoflurane and desflurane in a respiratory gas stream. In such applications, a separate sample stream is typically drawn from the patient respiratory gas assembly and directed into a sample chamber that is positioned on the optical path between the light source and detector.

It is particularly important in respiratory gas spectrometry that any significant absorbers of light at the center-wavelengths of interest that are on the optical pathway between the light source and detector be accounted for in calibration, and that the related calibration conditions be maintained during use. In this regard, the optical pathway(s) utilized in many respiratory gas spectrometers lie substantially within a sealed sample gas chamber. Further, given the responsivity needs of respiratory gas spectrometers, it is also important that the transmitted light reaching the detector be of an intensity that yields an acceptable signal to noise ratio.

SUMMARY OF THE INVENTION

In view of the foregoing, a primary objective of the present invention is to provide a gas spectrometer having a high degree of maintainable accuracy, and more particularly, which is capable of maintaining its initial calibration condition to reliably achieve the desired accuracy.

A related objective is to provide a highly accurate and responsive respiratory gas spectrometer that maintains and is readily serviceable to maintain its calibration conditions.

To achieve such objectives and realize other associated advantages, the gas spectrometer of the present invention recognizes the importance of maintaining calibration conditions in portions of the optical pathway(s) between a light source and detector that are within a contained area, yet outside of the sample gas region (i.e. between the light source and the sample gas region and/or between the sample gas region and the detector). More specifically, the present invention recognizes and addresses the need to maintain calibration conditions in the noted optical pathway portions, particularly in relation to one or more gaseous component(s) that correspond with one or more of the predefined gas component(s) to be measured in the sample gas stream or that "interfere" with such predefined gas component(s) (i.e. by absorbing radiation at the centerwavelength(s) of interest for such predetermined components).

In a respiratory gas spectrometer application, the present invention includes a housing assembly defining one or more enclosed, internal containment area(s), and an infrared radiation source and optical assembly positioned within the housing assembly to provide infrared radiation on one or more optical pathways. A sample gas chamber is positioned on at least one optical pathway within the housing assembly for containing and cycling a respiratory gas sample therethrough. A detector assembly is positioned within the housing assembly to receive the unabsorbed infrared radiation transmitted through the sample gas chamber. Finally, a gas removal assembly is interconnected to and is at least partially positionable within a corresponding internal containment area of the housing assembly for contacting and removing one or more predefined and undesired gas component types. The gas removal assembly may include a holder and at least one gas component removal material(s) retained by the holder. More particularly, the holder may include one or more openings through which an undesired gas component may diffuse and be absorbed by the removal material(s). The holder is selectively retractable relative to the housing assembly to facilitate periodic servicing/replacement of the gas component removal material(s) during field use of the spectrometer, thereby enhancing maintenance of the desired calibration conditions within the corresponding internal containment area of the housing assembly. Importantly, such maintenance can be readily achieved without disassembly of the housing assembly, thereby facilitating use and avoiding calibration complications that could arise upon disassembly/reassembly.

The gas removal material(s), or absorbent, utilized in the removal assembly may be advantageously selected to remove one or more gas component type(s) that correspond or interfere with one or more of the predefined gas components to be measured in the gas sample. In this regard it has been recognized that, in respiratory gas spectrometry, even relatively low carbon dioxide concentrations in the optical pathway lying outside of the respiratory gas sample chamber can potentially compromise the desired accuracy of $CO_2$ measurement of the device. This is particularly true where, for example, a significant portion of the overall length of the optical pathway lies outside of the gas sample chamber (e.g., more than at least about 90%). In order to maintain carbon dioxide levels at or below an initial calibrated level, a carbon dioxide absorbent, such as a granular soda lime material, may be utilized to absorb any $CO_2$ that is introduced into the corresponding internal containment area during use. In this regard, it is believed that adhesives, lubricants and other materials utilized in gas spectrometers may become sources of $CO_2$ during use.

It has also been recognized that, in certain situations, water vapor may accumulate in the optical path outside of the sample gas chamber, and that such water vapor may adversely impact the accuracy of the device, e.g., due to condensation on optical components within the gas spectrometer and resultant degradation of the signal to noise ratio at the detector assembly. To remove such undesired water vapor from the ambient atmosphere in the spectrometer, the present invention may also employ a water vapor desiccant, such as a ceramic-based molecular sieve or, silica gel.

Further, the gas removal material may include an absorbent such as charcoal chips to remove other potential contaminants from within the corresponding internal containment area. As indicated, the gas removal assembly is selectively retractable, and may be removable from the respiratory gas spectrometer housing in order to facilitate servicing. In one embodiment, the holder of the gas removal assembly includes a hollow, elongated body and an enlarged head. A portion of the body may be threaded for selective engagement/disengagement with a correspondingly threaded access opening in the housing assembly. An o-ring (e.g., of butyl rubber construction) or other appropriate sealing member may be interposed between the enlarged head and outer surface of the housing assembly. To facilitate periodic maintenance, an indicator may be included in the gas removal assembly or in a user interface (e.g. an electronic display or alarm) for alerting a user to replace the gas removal material on a predetermined basis. For example, a window may be disposed in the enlarged head of the holder to permit visual, external observation of granular soda lime material contained therein, such material changing from a white color to purple color upon becoming saturated by $CO_2$. Where water vapor sensing is desired an RH-sensitive paper test strip may be similarly disposed in the holder for external, visual inspection by a user. When a user interface is utilized as an indicator, servicing alert may entail periodic comparison (e.g., utilizing an on-board processor) between a detected/stored radiation intensity value(s) (e.g., at one or more predetermined center-wavelengths) established during calibration, and a subsequently detected radiation intensity value(s) (e.g., at the same center-wavelength(s)) after the unit is put into use. In this regard, the center-wavelength(s) should be within the wavelength range in which the gas component type(s) to be removed from the corresponding internal containment area displays absorbency characteristics. For example, where $CO_2$ removal and calibration condition maintenance is desired, the stored value(s) established during calibration and the detected value(s) obtained after the unit has been put into use may be at a center-wavelength(s) within the 4–5 micron range. As will be appreciated, the present invention provides an improved method for maintaining calibration conditions within a gas spectrometer, including in particular respiratory gas spectrometers used for determining the concentration of one or more predetermined components of a respiratory gas sample. More particularly, in the inventive method, a respiratory gas spectrometer may be assembled to define one or more containment area(s) and one or more optical pathways therewithin, and thereafter initially calibrated at desired calibration conditions (e.g., at the production facility to ensure accurate correlation between detected radiation intensity measurements and gas concentration determination (s)). Importantly, in conjunction with such assembly and calibration, an absorbent is exposed within one or more containment area(s) of the assembled gas spectrometer, wherein the absorbent is selected to remove one or more types of undesired gas component(s) that could be introduced during field use of the device (e.g., from adhesives or lubricants used in the device, out-gassing of sealing components used in the device, and/or leakage through components). By virtue of such exposure, the absorbent is capable of absorbing the undesired gas component type(s) from within the one or more internal containment area(s) on a continuous, ongoing basis so that the initial, desired calibration conditions within the spectrometer can be dynamically maintained, thereby enhancing continued accuracy of the device.

As noted above, the absorbent may comprise an appropriate material for removal of $CO_2$ (e.g., soda lime). Additionally, the absorbent may comprise a desiccant (e.g., a ceramic-based molecular sieve or silica gel) for removal of water vapor from within the internal containment area. Further, the absorbent may include an additional contaminant scrubber, such as activated charcoal chips for removal of undesired gas component(s) that may leak into or be generated within the internal containment area.

The inventive method further provides for the servicing and replacement of the absorbent from within an internal containment area, free from disassembly of the respiratory gas spectrometer. In this regard, the described arrangement also facilitates replacement of the absorbent without necessitating re-calibration of the spectrometer. More particularly, a holder for retaining an absorbent may be selectively withdrawn from a corresponding internal containment area via an access aperture in the housing assembly, serviced so as to replace depleted absorbent with fresh absorbent, and sealably reinserted into the internal containment area. Alternatively, a holder containing used absorbent may be selectively withdrawn and disposed of, and a new holder with fresh absorbent sealably inserted through the access aperture.

Relatedly, the inventive method may also provide for indicating to a user that the absorbent should be replaced. By way of example, such indication could be provided via a window in the absorbent holder (e.g. allowing external visual inspection of the color of an absorbent and/or RH-sensitive paper) or via an appropriate user interface (e.g., via a visual display and/or audible alarm indication). As noted hereinabove, the indication may entail an automatic or user initiated comparison between a stored value(s) (e.g., corresponding with a measured intensity value upon calibration at a selected, center-wavelength), and a corresponding measured value(s) during use (i.e. measured at the same selected, center- wavelength). Should such comparison result in a difference that exceeds a predetermined tolerance value, a user alert will be automatically generated.

As noted, for purposes of absorbent replacement, the inventive method may advantageously include the selective retraction and removal of a holder from within a corresponding internal containment area via an opening in the respiratory gas spectrometer. The holder may be advantageously sized for hand-held manipulation and ready reinsertion back into the opening upon replacement of the absorbent. In this regard, the holder is provided for ready, sealable engagement with gas spectrometer.

The holder is provided with at least one opening in that portion which is insertable into the internal containment area, wherein the undesired gas component type to be removed will diffuse through the opening from the ambient internal containment area for absorbance during use. The insertable holder portion may be readily defined by hollow, cylindrical configuration having an open end for receiving the absorbent and a screen for containment of the absorbent. A hollow insertable holder portion may also be employed that comprises a plurality of openings in the sidewalls thereof, such openings being sized so as to contain granular absorbent material therewithin, yet permit ready diffusion of the undesired gas component type(s) to be removed therethrough.

Numerous variations and advantages of the invention will be apparent to those skilled in the art. By way of example, a separate, retractable absorbent holder and access aperture in the housing assembly could be provided in one-to-one relation to each of a plurality of internal containment areas within the housing assembly. Alternatively, in such an arrangement, the absorbent provided to one of the containment areas (e.g., a smaller secondary area) may be contained in a porous bag or the like which is serviceable upon disassembly/reassembly.

DETAILED DESCRIPTION

Figure 1:
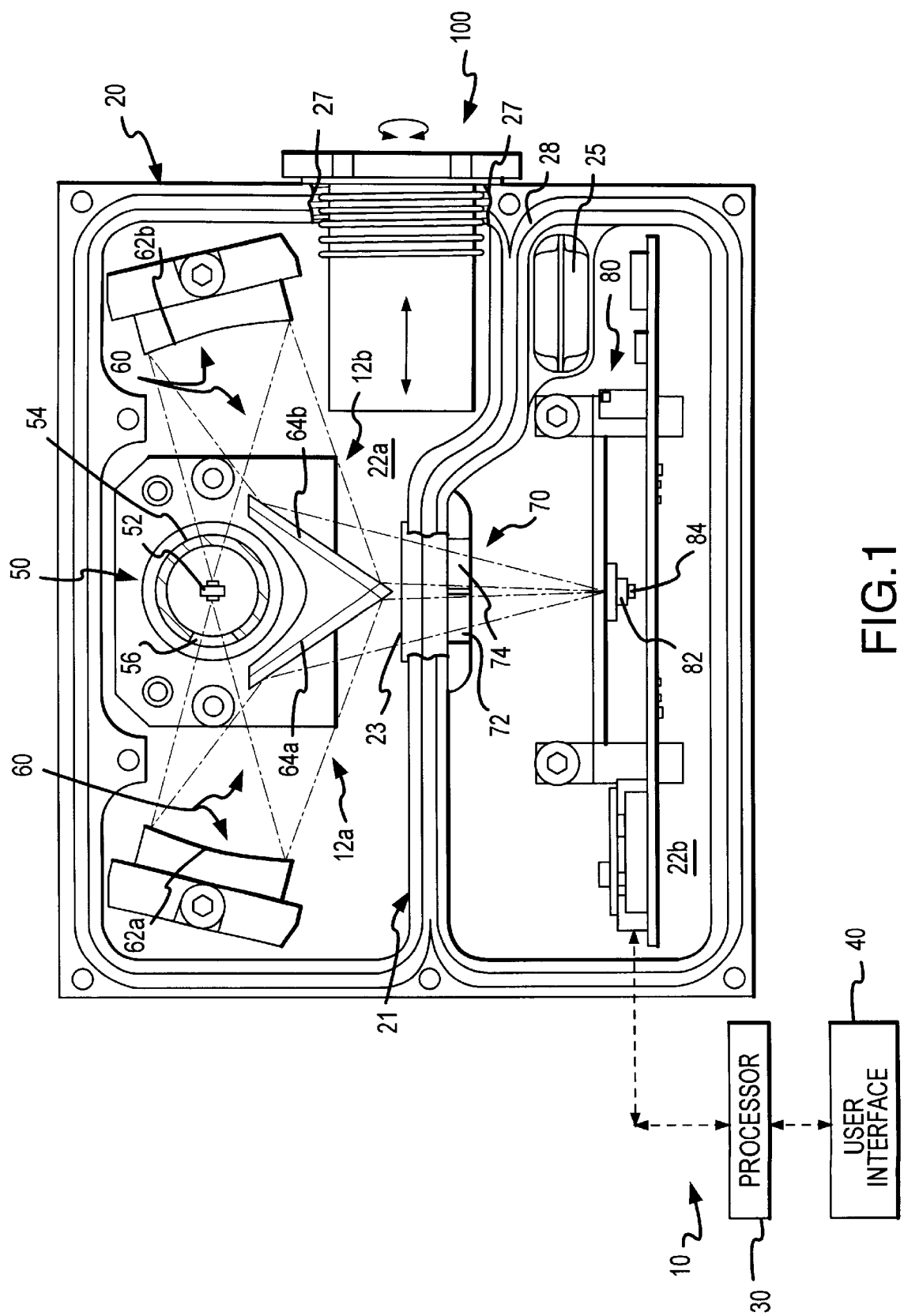
FIG. 1 is a top cross-sectional view of a housing assembly, shown in schematic combination with other components of a respiratory gas spectrometer embodiment of the present invention.

FIG. 1 illustrates a respiratory gas spectrometer embodiment 10, including a top cross-sectional, partially cut-away view of a housing assembly 20 shown in schematic combination with a processor 30 and user interface 40. The housing assembly 20 defines a primary enclosed, internal containment area 22a and a secondary, enclosed, internal containment area 22b. An infrared radiation assembly 50, optical assembly 60 and gas component removal assembly 100 are all at least partially disposed within the primary containment area 22a. A detector assembly 80 and gas sampling assembly 70 are each at least partially disposed in the secondary containment area 22b. The noted components cooperate to provide for accurate monitoring of the concentration of selected components within a respiratory gas stream cycled through gas sampling assembly 70. In this regard, the present invention may be readily utilized in a respiratory gas spectrometer as disclosed in U.S. patent application Ser. No. 08/403,161, now U.S. Pat. No. 5,731,581 hereby incorporated by reference in its entirety.

The infrared radiation assembly 50 includes an elongated, upstanding infrared source element 52 and a cylindrical, concentrically disposed light chopper 54. Chopper 54 includes a window 56 and is rotatable about source element 52 for alternatively transmitting radiation on first and second optical paths 12a and 12b, at least partially defined by optical assembly 60.

The optical assembly 60 includes first and second spherical mirrors 62a and 62b, for collecting and directing radiation from source element 52 on first and second optical paths 12a and 12b, respectively. The resultant, converging optical beams on paths 12a and 12b are separately redirected via first and second flat mirrors 64a and 64b, respectively.

As illustrated, the housing assembly 20 includes an internal wall 21 defining the separate containment areas 22a and 22b. Internal wall 21 is provided with an opening therethrough so as to receive gas sampling assembly 70 and transparent window member 23, as shown by a partially cut-away portion of wall 21 in FIG. 1. Both window member 23 and gas sampling assembly 70 are positioned on optical paths 12a, 12b. The gas sampling assembly 70 includes a gas sample chamber 72 and reference gas chamber 74 disposed relative to optical assembly 60 such that the first converging beam on path 12a passes through opposing, transparent windows of gas sample chamber 72, and the second converging beam on path 12b passes through opposing, transparent windows of the reference gas chamber 74. The gas sample assembly 70 is interconnected to gas flow lines (not shown) for continuously cycling a sample stream of respiratory gas from a patient through the gas sample chamber 72.

The detector assembly 80, includes an upstanding linear variable filter (not shown), an adjacent $CO_2$ band pass filter 82 positioned thereabove, and an upstanding linear array of pyro-electric detector elements 84 positioned behind the linear variable filter and band pass filter 82. The detector assembly 80 is positioned so that non-absorbed radiation transmitted through gas sample chamber 72 and reference gas chamber 74 on paths 12a and 12b, respectively, is filtered by the linear variable filter and the band pass filter 82, and detected by linear detector array 84. As will be appreciated, the detected radiation will not include radiation that is absorbed by gas component(s) present along paths 12a and 12b, including in particular gas component(s) contained within chamber 72. In operation, the linear variable filter will simultaneously filter transmitted radiation in a spatially distributed manner across a wavelength range, including the 7–10 micron range. The 7–10 micron range covers sub-ranges across which many anesthetic gas agents will display unique radiation absorbance characteristics. The $CO_2$ band pass filter 82 will pass unabsorbed radiation in the 4–5 micron range, which range encompasses that within which $CO_2$ displays unique radiation absorbance characteristics. By utilizing detector array 84 to simultaneously obtain intensity measurement values at predetermined center-wavelengths across the 7–10 and 4–5 micron wavelength range, the resultant data can be provided to processor 30 for multi-variate statistical processing, and determination of the concentration of one or more anesthetic gas agents and $CO_2$ for visual or audible output/alarm by user interface 40. The described arrangement is highly robust in terms of accuracy and responsivity. As can be appreciated, the continued accuracy of the gas spectrometer 10 during field use depends in part upon maintenance of predetermined calibration conditions within housing assembly 20.

In this regard, gas component removal assembly 100 is disposed partially within the primary internal containment area 22a for removing one or more types of undesired gas components, e.g., $CO_2$, from the internal containment area 22a during field use of the respiratory gas spectrometer 10. Additionally, an optional gas removal member 25 may be provided in secondary containment area 22b for removing one or more types of undesired gas components from containment area 22b. By way of example, gas removal member 25 may be a porous bag of fiber construction filled with a $CO_2$ gas removal material (e.g. granular soda lime).

Figure 2A:
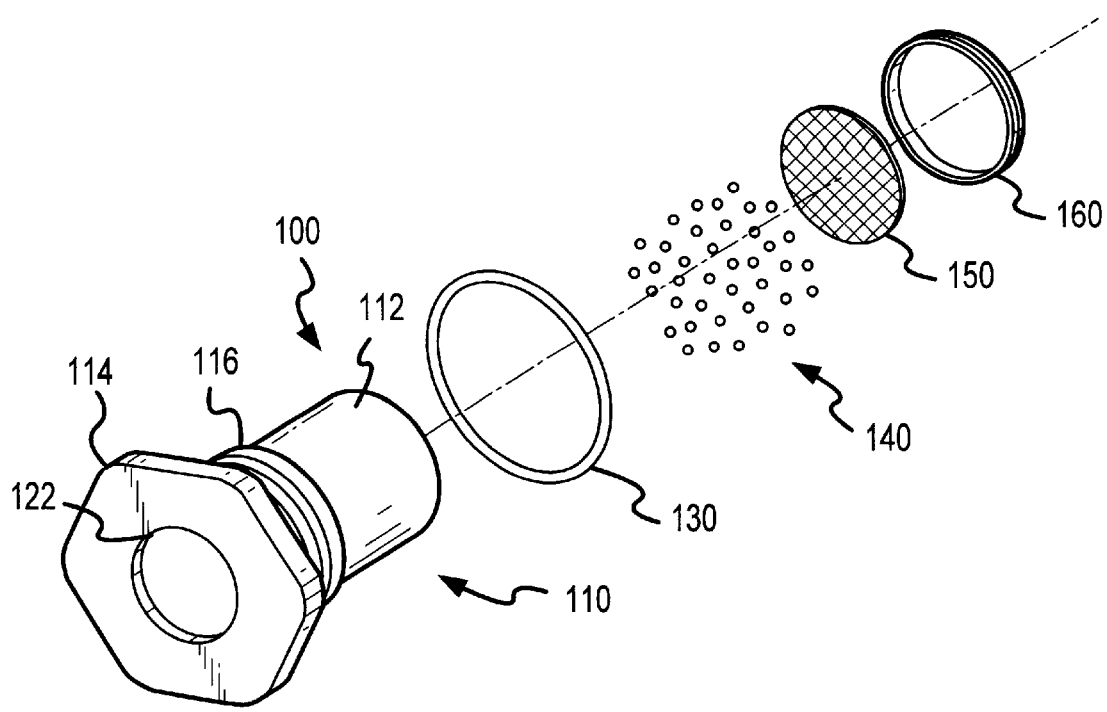
FIGS. 2a and 2b illustrate a perspective, exploded assembly view of a gas component removal assembly and a side view of the gas component removal assembly, respectively.
Figure 2B:
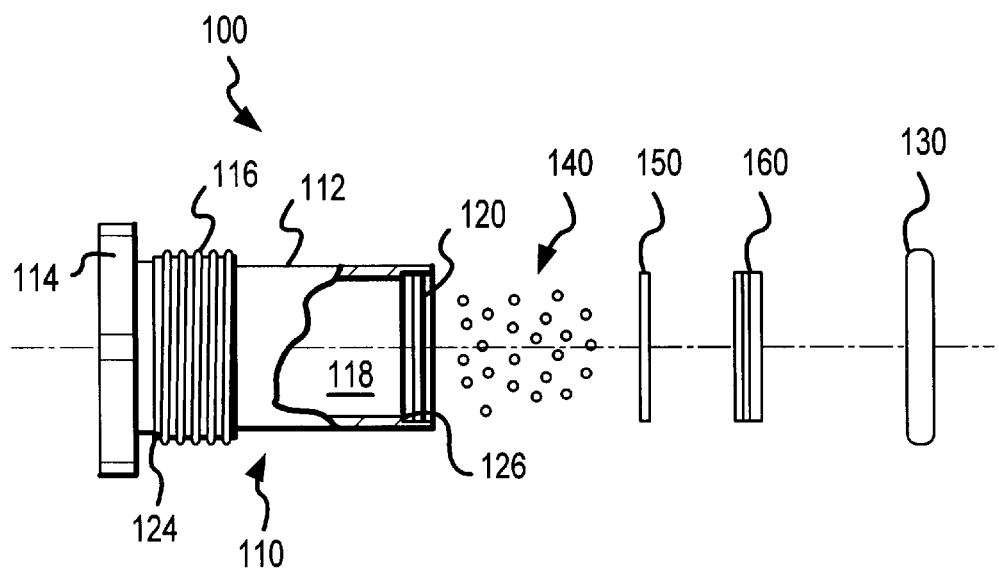

As illustrated, gas removal assembly 100 is provided for selective, sealable engagement/disengagement with housing assembly 20. This arrangement advantageously facilitates selective servicing of the gas component removal assembly 100 during field operation, free from disassembly of housing assembly 20. More particularly, and as illustrated in FIGS. 2a and 2b, gas component removal assembly 100 may comprise an open-ended, metal holder 110 having a barrel 112 and enlarged, close-ended head 114. Enlarged head 114 may be of a hexagonal configuration adapted for engagement with a wrench tool. In this regard, barrel 112 includes an outer threaded portion 116 for engagement/disengagement with a threaded opening 27 of housing assembly 20.

The gas removal assembly 100 further includes an o-ring 130, positionable over a seat portion 124 of barrel 112, for sealing the interface between the enlarged head 114 and the outside surface of housing assembly 20 during use. By way of example, o-ring 130 may comprise butyl rubber, which has been found to be of particular advantage due to its low $CO_2$ and water vapor permeability properties. Alternatively, a fluorocarbon material such as viton may be employed in o-ring 130. Gas removal assembly 100 also includes a gas removal absorbent material 140 contained within internal space 118 of holder 110. In this regard, the absorbent material 140 is preferably in a loose, granular or other like form to increase the exposed surface area for absorption. The absorbent material 140 may include a granular soda lime material, which has been recognized as particularly effective for the removal of $CO_2$ from the containment space 22a upon passive contact. In this regard, by providing a transparent window 122 in head 114 of holder 110, saturation of a granular soda lime absorbent material can be visually indicated external to housing assembly 20 since such absorbent can be provided to change color upon use (e.g. from white to purple upon becoming saturated with $CO_2$).

In situations where it is desirous to remove water vapor, the gas removal absorbent 140 may comprise a desiccant such as a ceramic-based molecular sieve or silica gel. In such cases, an RH-sensitive paper may be disposed in holder 110 for visual observation via window 122 to indicate when the desiccant is saturated and in need of replacement (i.e. when RH-sensitive vapor changes color). To remove organics, it may also be desirable to employ an absorbent such as activated carbon (e.g., charcoal chips).

To retain the loose gas component removal absorbent 140 within the open end of the barrel portion 112 of holder 110 during use, yet permit passive gas contact with the gas component removal material 140, a porous screen 150 and threaded retainer ring 160 are positioned within the internally threaded region 120 of holder 110. As illustrated, screen 150 is restricted between retainer ring 160 and an internal ledge 126 provided within the barrel 112 of holder 110. In another arrangement, barrel 112 could be integrally provided with small holes along and about its length or could otherwise be constructed from a porous material to enhance diff-usion of the undesired gas component(s) therethrough.

Referring again now to FIG. 1, it can be seen that the barrel 112 of holder 110 of removal assembly 100 is sized and positioned relative to the other components of the respiratory gas spectrometer 10 so that it does not cross or otherwise impede any portion of the first optical path 12a or second optical path 12b. Further, holder 110 is positioned so that any $CO_2$ or other undesired component(s) that may be introduced into internal containment area 22a during field operation may readily pass directly into the open end of barrel 112 and contact the gas removal material 140 contained therewithin.

Figure 3A:
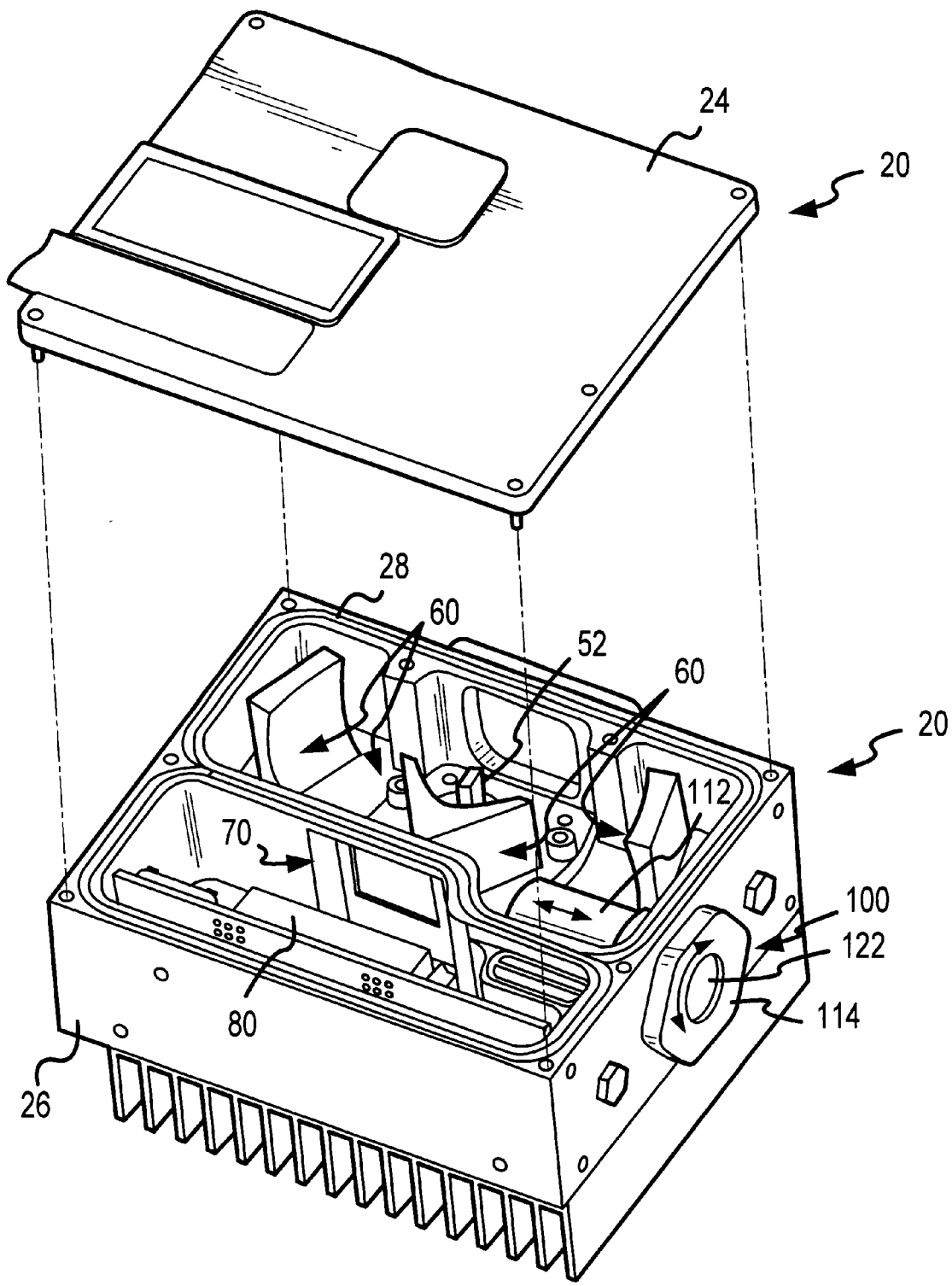
FIGS. 3a and 3b illustrate elevated front perspective and elevated rear perspective views, respectively, of the housing assembly of the embodiment of FIG. 1.
Figure 3B:
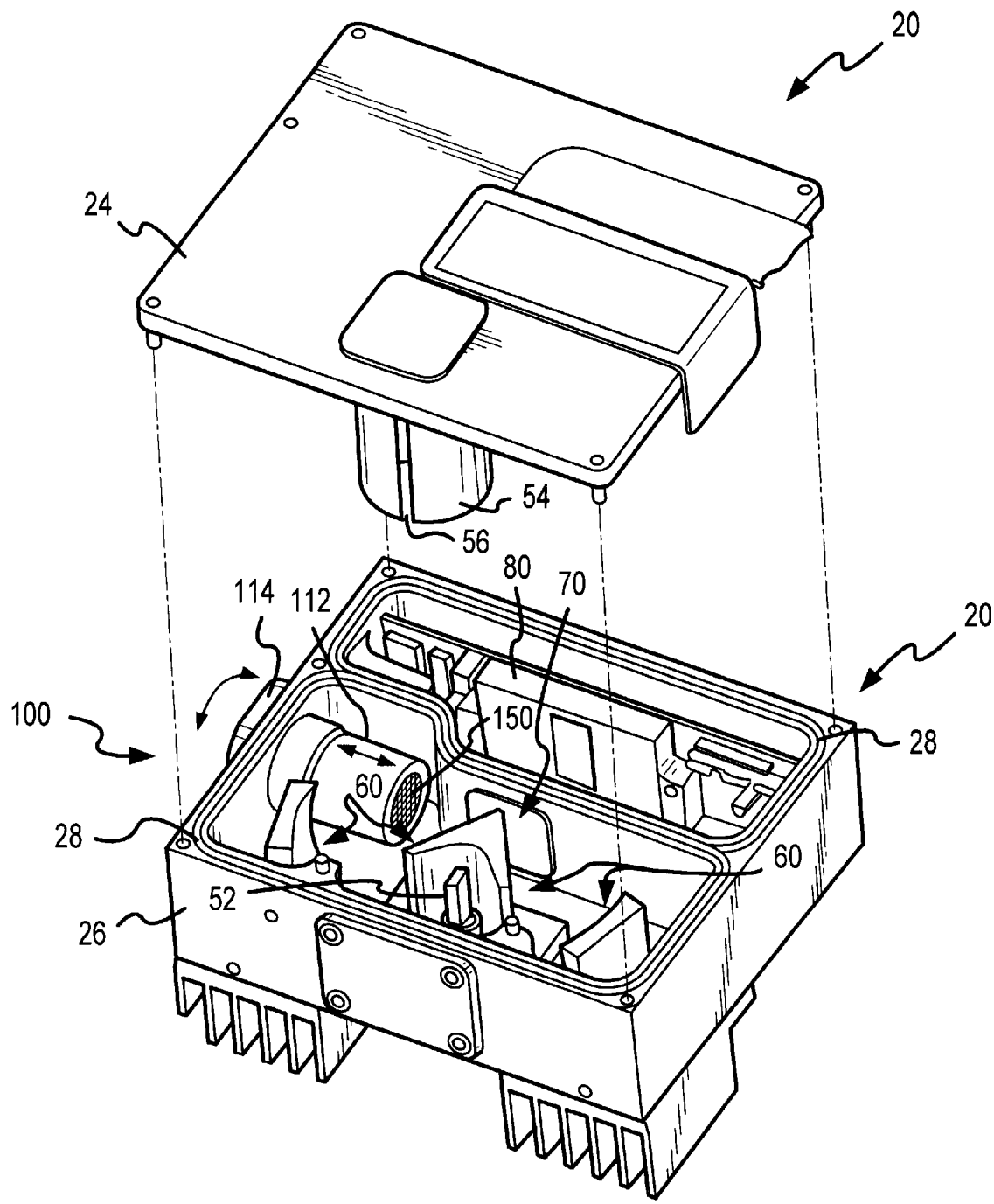

FIGS. 3a and 3b provide additional views of the above-noted components within housing assembly 20. As illustrated, the gas removal assembly 100 is positioned outside of the optical pathways. FIGS. 3a and 3b also show that housing assembly 20 may be principally defined by a top member 24 and bottom member 26, which may be sealably assembled together. In this regard, a sealing member (e.g. a resilient, continuous gasket) 28 may be provided at the interface between the top member 24 and bottom member 26 of housing assembly 20, and the two members may be securely interconnected via screws and threaded holes about their periphery. Upon assembly of the respiratory gas spectrometer embodiment 10, including interconnection of the top and bottom members 24 and 26 of housing assembly 20, the internal containment areas 22a, 22b are defined therewithin. As illustrated in FIG. 1, over 90% of the length of optical paths 12a, 12b from source 52 to detector assembly 80 lies outside chambers 72, 74. Further, the majority of such optical paths 12a and 12b lie within the primary containment area 22a serviced by gas removal assembly 100. In conjunction with the assembly of the spectrometer 10, the gas removal assembly 100 may be inserted into threaded opening 27 within the bottom member 26 and rotated relative thereto for threading engagement between threaded portion 116 on the barrel 112 of the holder 110 and the threaded opening 27. In this regard, it is noted that the threaded portion 116 on the barrel 112 of holder 110 is spaced from the enlarged head 114 such that the oring 130 is received by intermediate portion 124. As such, threaded rotation of holder 110 relative to the threaded opening 27 will be properly restricted when the end of threaded portion 116 is reached so as to allow appropriate compression of o-ring 130 against the outer wall of housing assembly 20 to achieve sealing, yet not over-stress the o-ring 130 due to over-rotation of holder 110 causing over- compression of o-ring 130.

Upon assembly of the respiratory gas spectrometer 10, initial calibration can be completed at the production facility (at desired calibration conditions, within containment spaces 22a and 22b). By way of example, such calibration may typically include obtaining radiation measurements at numerous center-wavelengths and processing the measurement values via processor 30 to ensure that accurate determinations of predefined respiratory gas component(s) will be obtained when the spectrometer 10 is introduced into field use.

After final calibration, the respiratory gas spectrometer 10 is ready for field use, wherein the gas removal material 140 is continuously exposed within the internal containment area 22a. By virtue of such exposure the undesired gas components which are to be removed from containment area 22a are free to diffuse through screen 150 for absorption by the absorbent material 140. Such diffusion will continue on an ongoing basis as undesired gaseous components are introduced into the internal containment space during use. As will be appreciated, barrel 112 may be constructed from a porous material or may otherwise comprise small holes about and along the length thereof to facilitate $CO_2$ diffusion therethrough.

The processor 30 may be adapted to automatically provide a signal to the user interface 40 so as to indicate to a user when the gas removal material 140 should be replaced or tested for replacement. Such indication may be provided in the way of a visual display and/or audible alarm. The triggering of such a signal may be based on periodic comparison between calibration and in-use measurement values obtained at one or more center-wavelengths.

To service the respiratory gas spectrometer 10, a user simply rotates the gas removal assembly 100 (e.g., with the use of a wrench tool), and withdraws the gas removal assembly 100 from housing assembly 20. A gas removal assembly 100 with "fresh" gas removal material 140 contained therein may then be screwed into housing assembly 20. Alternatively, the "old" gas removal assembly 100 may be serviced for reuse. Specifically, retainer ring 160 may be unscrewed from the barrel 112 of the holder 110, the screen 150 removed, and the gas removal material 140 disposed of. The fresher replacement gas removal material 140 may then be introduced and the gas removal assembly 100 reassembled. Gas removal assembly 100 may then be easily positioned back through threaded opening 27 of the housing assembly 20. As will be appreciated, the described arrangement thus avoids disassembly of the housing assembly 20 for servicing purposes, and does not necessitate re-calibration of the device.

Numerous additional embodiments and variations of the invention will be apparent to those skilled in the art and are intended to be within the scope of the present invention, as defined by the following claims.

What is claimed is:

1. A respiratory gas analyzer for determining the concentration of one or more predefined components of a respiratory gas sample, comprising:

a housing assembly defining an internal containment area;

at least one infrared radiation source positioned within said housing assembly;

an optical assembly positioned within said housing assembly for directing infrared radiation from the infrared source on one or more optical paths;

a sample gas chamber, positioned on at least one optical path within said housing assembly, for receiving a respiratory gas sample therewithin;

a detector assembly, positioned within said housing assembly, for detecting the intensity of infrared radiation passing through said sample gas chamber on said at least one optical path and for providing an output signal in relation thereto, wherein said output signal is employable to determine the concentration of one or more of said predefined components of said respiratory gas sample; and a gas removal assembly at least partially positioned within the containment area defined by said housing assembly for removing one or more selected gas component types from said internal containment area of said housing assembly, said gas removal assembly having a holder and removal material held therein, wherein said removal assembly is selectively retractable relative to and sealably engageable with said housing assembly for periodic replacement of said removal material.

2. A respiratory gas analyzer, as recited in claim 1, wherein said removal material is in a particulate form and said holder includes:

a hollow portion for containing the particulate removal material and being selectively positionable within said internal containment area during use; and one or more openings into said hollow portion for diffusion of said one or more selected gas component types therethrough during use.

3. A respiratory gas analyzer, as recited in claim 2, wherein said one or more openings are of a maximum width that is less than a maximum width of the particulate gas removal material.

4. A respiratory gas analyzer, as recited in claim 2, said holder further including an enlarged head adjoined to the hollow portion for interface with an outer surface of the housing assembly during use; and a sealing member positionable between said enlarged head and the outer surface of said housing assembly during use.

5. A respiratory gas analyzer, as recited in claim 2, wherein said hollow portion of said holder includes an outer threaded portion, and wherein said housing assembly includes a correspondingly threaded opening for threadably receiving said outer threaded portion of said holder.

6. A respiratory gas analyzer, as recited in claim 1, wherein one of said predefined components of the respiratory gas sample is $CO_2$, and wherein said removal material is selected for absorption of $CO_2$ from within said internal containment area.

7. A respiratory gas analyzer, as recited in claim 6, wherein said removal material comprises granular soda lime.

8. A respiratory gas analyzer, as recited in claim 6, wherein said at least one optical path has a length from said source to said detector assembly, and wherein at least ninety percent (90%) of said length is located outside of said sample gas chamber.

9. A respiratory gas analyzer, as recited in claim 1, wherein said removal material includes a desiccant for removal of water vapor from within the internal containment area.

10. A respiratory gas analyzer, as recited in claim 1, wherein an elongated portion of said holder extends inward into said internal containment area and is positioned outside of said one or more optical paths.

11. A method for maintaining calibration of a respiratory gas spectrometer for determining concentration of one or more predetermined components of a respiratory gas sample, comprising:

assembling a respiratory gas spectrometer, wherein an internal containment area and one or more optical paths therewithin are defined;

exposing an absorbent within said internal containment area, wherein said absorbent is selected to remove $CO_2$;

initially calibrating the respiratory gas spectrometer under desired calibration conditions within said containment area;

absorbing $CO_2$ into said absorbent from within the internal containment area during use, wherein said desired calibration condition is maintained; and replacing said absorbent free from disassembly of the respiratory gas spectrometer.

12. A method as recited in claim 11, further comprising the step of:

indicating to a user when said absorbent should be replaced.

13. A method as recited in claim 11, wherein said replacing step includes:

removing a holder, containing said absorbent, from said internal containment space;

replacing used absorbent within said holder with new absorbent; and reinserting said holder into said internal containment area.

14. A method as recited in claim 13, wherein said removing step includes:

withdrawing said holder through an opening in said respiratory gas spectrometer wherein said opening is sized for mating engagement with said holder.

15. A method as recited in claim 14, wherein said reinserting step includes:

establishing a seal in said opening between said holder and said respiratory gas spectrometer.

16. A method as recited in claim 15, wherein each of said withdrawing and reinserting steps include:

rotating said holder relative to said respiratory gas spectrometer.

\* \* \* \* \*